United States Patent
Lien et al.

(10) Patent No.: US 9,480,722 B2
(45) Date of Patent: Nov. 1, 2016

(54) METHOD OF ALLEVIATING OR TREATING PERIODONTAL DISEASE

(75) Inventors: Hsiu-Man Lien, Taichung (TW); Chia-Chang Chen, Taichung (TW); Chin-Jui Tseng, Taichung (TW)

(73) Assignee: Yushen Biotechnology & Medical Co., Ltd., Taichung (TW)

( * ) Notice: Subject to any disclaimer, the term of this patent is extended or adjusted under 35 U.S.C. 154(b) by 1075 days.

(21) Appl. No.: 13/411,704

(22) Filed: Mar. 5, 2012

(65) Prior Publication Data

US 2013/0189296 A1 Jul. 25, 2013

(30) Foreign Application Priority Data

Jan. 20, 2012 (TW) .............................. 101102379 A

(51) Int. Cl.
*A61K 36/07* (2006.01)
*A61K 9/00* (2006.01)

(52) U.S. Cl.
CPC ............... *A61K 36/07* (2013.01); *A61K 9/006* (2013.01)

(58) Field of Classification Search
None
See application file for complete search history.

(56) References Cited

U.S. PATENT DOCUMENTS

| | | | |
|---|---|---|---|
| 4,981,693 A * | 1/1991 | Higashi et al. | |
| 5,990,100 A * | 11/1999 | Rosenberg et al. | |
| 7,109,226 B2 * | 9/2006 | Yamazaki et al. | |
| 7,501,454 B2 * | 3/2009 | Liu | C07C 403/02 514/690 |
| 2009/0048330 A1 * | 2/2009 | Hattori | C07D 207/444 514/425 |

FOREIGN PATENT DOCUMENTS

| KR | 20020055546 A | * | 7/2002 |
|---|---|---|---|
| TW | 201200144 | | 1/2012 |

OTHER PUBLICATIONS

"Mr Kent's ChemistryPage". Retrieved from the Internet on: May 27, 2016, <Retrieved from: URL: http://www.kentchemistry.com/links/bonding/LikeDissolveslike.htm>.*
Geethangili et al. Food Chemistry 119 (2010) 149-153.*
Al Asqah et al. Can J Gastroenterol vol. 23 No. 3 Mar. 2009, 177-179.*
Myrella Lessio Castro, et al.; Identification of a bioactive compound isolated from Brazilian propolis type 6; Bioorganic & Medicinal Chemistry, 17 (2009) 5332-5335.
Mi-Sun Kang, et al.; Inhibitory Effect of Methyl Gallate and Gallic Acid on Oral Bacteria; The Journal of Microbiology, Dec. 2008, p. 744-750.

* cited by examiner

*Primary Examiner* — Amy L Clark
(74) *Attorney, Agent, or Firm* — Fishman & Associates, LLC.

(57) ABSTRACT

A composition for use in inhibiting or killing *Porphyromonas gingivalis*, comprising an effective amount of *Antrodia camphorata* powder or extract and acceptable carriers thereof for inhibiting or killing *Porphyromonas gingivalis*. Also provided is a method of inhibiting or killing *Porphyromonas gingivalis* by using aforementioned composition. Further provided is a method of alleviating or treating diseases derived from *Porphyromonas gingivalis* by administrating a therapeutically effective amount of aforementioned composition. The *Antrodia camphorata* extract in accordance with the present invention have been proved having the efficacy of inhibiting or killing *Porphyromonas gingivalis*, and thus can be easily applied to various fields, particularly, health foods, drinks and applications of daily supplies. Moreover, advantages in accordance with the present invention include no side effects, easy fabricating and low cost.

2 Claims, 3 Drawing Sheets

METHOD OF ALLEVIATING OR TREATING PERIODONTAL DISEASE

BACKGROUND OF THE INVENTION

1. Field of the Invention

The present invention relates to a composition for use in inhibiting or killing *Porphyromonas gingivalis*. The present invention also relates to pharmaceutical composition for use in alleviating or treating the diseases derived from *Porphyromonas gingivalis*.

2. Description of the Prior Arts

According to statistics of the Taiwan Dental Association, there are more than 90% adults suffering from periodontal disease, wherein the main cause of periodontal disease is periodontal bacteria infecting gingival tissue or alveolar bone.

As currently known, the main pathogenic periodontal bacteria are *Actinobacillus actinomycetemcomitans* (Aa), *Porphyromonas gingivalis* (Pg), *Fusobacterium nucleatum* (Fn), and *Bacteroides forsythus* (Bf). The glycoprotein of the saliva component would form a film on surface of teeth in oral cavity, thus said periodontal bacteria are liable to adhere on surface of teeth to form plaques. The plaques would combine with calcium of saliva component, then gradually become harder, and form dental calculus. Moreover, fimbriaes of the periodontal bacteria would secrete protease to decompose interior gingiva, and then destroy the gingival tissues and the bone of teeth to cause osteoporosis. *Porphyromonas gingivalis* is a gram-negative bacteria growing in anaerobic environment, which is not only common in oral cavity, but also grows in upper gastrointestinal tract, respiratory tract and colon. The current research states *Porphyromonas gingivalis* would induce matrix metalloproteinases (MMPs) to enhance inflammation, and lipopolysaccharide (LPS) on surface of bacteria cell wall also induce overly immune response of the host and induce interleukin production, thus, lead into worsen rheumatoid arthritis. *Porphyromonas gingivalis* even circulates in blood streams all over the body, leading into myocardial infarction, arteriosclerosis, thromboangiitis obliterans (TAO), bacterial pneumonia and diabetes.

Existing treatments used for periodontal disease comprise mechanical and chemical control methods. The mechanical control method includes using toothbrush and floss, ultrasonic scaling and root planning. Also under post-operation or special situation, said mechanical control method can be adopted in coordination with toothpaste and mouthwash of chemical treatment to assist controlling periodontal disease. The toothpaste and mouthwash currently available on market mostly comprise ethanol or chlorhexidine (CHX) to reduce and inhibit oral bacteria proliferation, wherein high concentration ethanol would destroy oral and tongue mucosa to increase the permeability of virus or carcinogen; and chlorhexidine, though being of better inhibition effect, has side effects like teeth and tongue dyeing, bad tasting, temporary dysgeusia, temporary epithalaxy, and increasing dental calculus deposition.

Despite the aforementioned treatments by western medicine, the main periodontal disease treatment by Chinese medicine is taking Chinese herb to exclude "dampness-heat (shi-re)" within the interior body in coordination with "strengthening spleen and stomach (jian-pi-wei)" to alleviate gingival inflammation. *Antrodia camphorata*, one of the most used Chinese herbs, has active ingredients composed of triterpenoids, polysaccharides, superoxide dismutase (SOD) and adenosine. Recent studies show active ingredients have efficacy of antitumor, antiinflammation, antihypertension, hypoglycemic, and lowering cholesterol; however, the current technique does not disclose *Antrodia camphorata* can be used for oral health caring, and is effective for killing specific anaerobic bacteria or facultative bacteria.

SUMMARY OF THE INVENTION

Given that the aforesaid drawbacks of the prior art, the present invention provides a composition for use in inhibiting or killing *Porphyromonas gingivalis*, and applications thereof. The composition comprises an effective amount of *Antrodia camphorata* powder or *Antrodia camphorata* extract and acceptable carriers thereof for inhibiting or killing *Porphyromonas gingivalis*. In comparison with antibiotics of prior art, the *Antrodia camphorata* powder or extract thereof of the present invention is used in inhibiting *Porphyromonas gingivalis* by lower concentration. The *Antrodia camphorata* extract is obtained from natural plants, which is safer and do not have said side effects of aforementioned alcohol or chlorhexidine.

To achieve said objective, the present invention provides a composition for use in inhibiting or killing *Porphyromonas gingivalis*, comprising an effective amount of *Antrodia camphorata* powder or extract and acceptable carriers thereof for inhibiting or killing *Porphyromonas gingivalis*, wherein the *Antrodia camphorata* extract is extracted from *Antrodia camphorata* by water, organic solvent or a combination thereof.

According to the present invention, the term "effective amount of *Antrodia camphorata* powder or extract for inhibiting or killing *Porphyromonas gingivalis*" as used herein refers to a dosage capable of alleviating or stopping the growth of *Porphyromonas gingivalis*, and even killing *Porphyromonas gingivalis*. According to the present invention, the effective amount for inhibiting growth of *Porphyromonas gingivalis* is determined by ex vivo minimal inhibitory concentration (MIC) of *Porphyromonas gingivalis*; the effective amount for killing *Porphyromonas gingivalis* is determined by ex vivo minimal bactericidal concentration (MBC) of *Porphyromonas gingivalis*.

According to the present invention, *Antrodia camphorata* is cultured by various type of culturing means for instance, solid-state incubation, liquid culture or a combination thereof to obtain *Antrodia camphorat* products in any form. Any *Antrodia camphorat* product having activity of inhibiting or killing *Porphyromonas gingivalis* is suitable for the present invention, including, for example, but not limited to, mycelium and sporophore of the *Antrodia camphorata*.

Preferably, said *Antrodia camphorata* extract is extracted from sporophore of the *Antrodia camphorata* by water or organic solvent, wherein the organic solvent includes, but not limited to, alcohol, ester, alkyl, or alkyl halides.

According to the present invention, said *Antrodia camphorata* extract is extracted from sporophore of the *Antrodia camphorata* by an aqueous ethanol solution at any concentration.

Preferably, aqueous ethanol solutions are, for example, but not be limited to, 20%, 50% or 95% (v/v) aqueous ethanol solutions.

Preferably, said *Antrodia camphorata* extract is extracted from sporophore of the *Antrodia camphorata* by 95% aqueous ethanol solution.

According to the present invention, the term "acceptable carriers" as used herein refers to: if a pharmaceutical composition is oral formulation, the carriers could protect the pharmaceutical composition from dissolution and digestion before reaching active site to lose effect, and/or enhance the delayed release of active compound from and the efficacy of the pharmaceutical composition.

Preferably, said effective amount of *Antrodia camphorata* extract for inhibiting or killing of *Porphyromonas gingivalis* is between 1 µg/ml and 16 µg/ml. Particularly, said effective amount of *Antrodia camphorata* extract for inhibiting or killing of *Porphyromonas gingivalis* is between 2 µg/ml and 4 µg/ml.

In another aspect, the present invention provides a method of inhibiting or killing *Porphyromonas gingivalis* by using aforementioned composition comprising:

providing a composition; and contacting the composition with *Porphyromonas gingivalis* such that *Porphyromonas gingivalis* is inhibited or killed, wherein the composition comprises the effective amount of *Antrodia camphorata* powder or extract for inhibiting or killing *Porphyromonas gingivalis*.

Preferably, said effective amount of *Antrodia camphorata* extract for inhibiting or killing of *Porphyromonas gingivalis* is between 1 µg/ml and 16 µg/ml. Particularly, said effective amount of *Antrodia camphorata* extract for inhibiting or killing *Porphyromonas gingivalis* is between 2 µg/ml and 4 µg/ml.

In yet another aspect, the present invention provides a method of alleviating or treating diseases derived from *Porphyromonas gingivalis*, comprising:

administrating a therapeutically effective amount of aforementioned composition to a subject in need, wherein the diseases derived from *Porphyromonas gingivalis* include periodontal disease, cardiovascular disease, and immune disease.

Preferably, said periodontal disease includes, but not limited to, paradentitis and gingivitis.

Preferably, said cardiovascular disease includes, but not limited to, myocardial infarction, infective endocarditis, arteriosclerosis, and thromboangiitis obliterans (TAO).

Preferably, said immune disease includes, but not limited to, rheumatoid arthritis, lupus erythematosus, psoriasis, and inflammatory bowel disease.

According to the present invention, the term "alleviating or treating" as used herein refers to the pharmaceutical compositions could cure or relieve said diseases or symptoms.

The pharmaceutical composition in accordance with the present invention could be made into, including but not limited to, foods, clean supply and drinks. In a preferred embodiment, toothpaste and mouthwash are included.

The *Antrodia camphorata* extract in accordance with the present invention have been proved having the efficacy of inhibiting or killing *Porphyromonas gingivalis*, and used as a novel composition of anti-*Porphyromonas gingivalis* to alleviate or treat the diseases derived from *Porphyromonas gingivalis*, wherein the diseases include periodontal disease, cardiovascular disease and immune disease. The *Antrodia camphorata* extract can be obtained easily because it could be obtained from sporophore of *Antrodia camphorata* native plants. Moreover, the *Antrodia camphorata* extract purified and separated by said methods in accordance with the present invention have no side effects as chemical synthesis does, and thus can be easily applied to various fields, particularly, health foods, drinks and applications of other daily supplies.

DETAILED DESCRIPTION OF THE PREFERRED EMBODIMENTS

Figure 1:
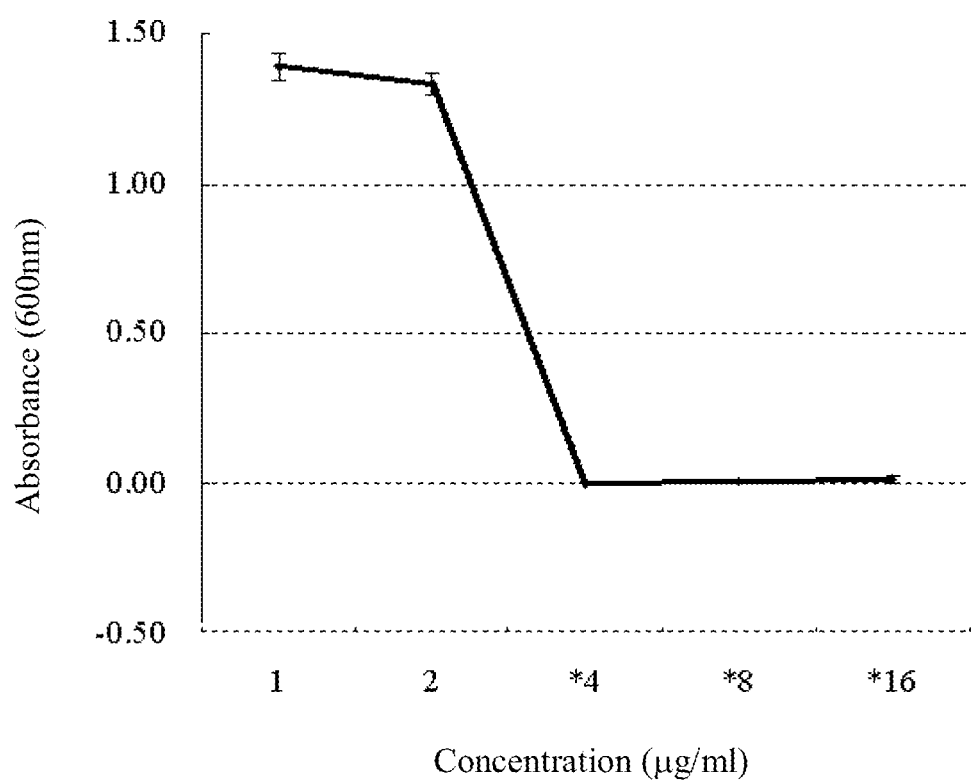
FIG. 1 illustrates the graph of inhibitory effect of *Antrodia camphorata* extract at various concentrations (1 µg/ml, 2 µg/ml, 4 µg/ml, 8 µg/ml and 16 µg/ml) on inhibiting *Porphyromonas gingivalis*.

Other objectives, advantages and novel features of the invention will become more apparent from the following detailed description when taken in conjunction with the accompanying drawings.

EXAMPLE

Material and method

1. Chemical Drugs and Reagents

Chlorhexidine digluconate (CHX) was purchased from Alfa aesar Corp.

Cysteine HCl was purchased from Sigma Corp. Hemin® was purchased from Fluka Corp. Brain heart infusion agar (BHI agar) was purchased from BD Corp. Brain heart infusion broth (BHI broth) was purchased from BD Corp. Yeast extract (YE) was purchased from BD Corp. Vitamin K1 was purchased from Sigma Corp. Defibrinated sheep blood was purchased from Bio-protech Corp. Dimethyl sulfoxide (DMSO) was purchased from Sigma Corp. 95% EtOH was purchased from Sigma Corp.

2. Preparation of Supplemented Brain Heart Infusion Agar (sBHI Agar) and Supplemented Brain Heart Infusion Broth (sBHI Broth)

5.2 g brain heart infusion agar and 0.5 g yeast extract were added to water to 100 ml in volume, then placed at 50° C. after sterilization, and added with 5% defibrinated sheep blood to serve as a supplemented brain heart infusion agar. 3.7 g brain heart infusion broth and 0.5 g yeast extract were added to water to 100 ml in volume, then placed at room temperature after sterilization, and added with 0.05 g Cysteine HCl, 1 ml hemin solution and 20 µl vitamin K1 to serve as a supplemented brain heart infusion broth.

3. Preparation of *Antrodia camphorata* Extract 10 g dry powder of wild *Antrodia camphorata* (from Xinyi Township, Nanton County, Taiwan) was added to 100 ml of 95% ethanol, and extracted for 48 hours at 29° C., and then preserved at −80° C. after vacuum rotary concentration and vacuum frozen-drying to obtain an *Antrodia camphorata* 95% ethanol extract. Wherein said dry powder of wild *Antrodia camphorata* was made from the following steps: providing sporophore of wild *Antrodia camphorata*, drying the sporophore of *Antrodia camphorata*, and grounding the dried sporophore of *Antrodia camphorata* to obtain the dry powder of *Antrodia* camphorata.

4. Microbial Material

*Porphyromonas gingivalis* was purchased from Food Industry Research and Development Institute (FIRDI) (Hsin-chu, Taiwan) with the accession number BCRC 14417. After thawing from frozen tube, *Porphyromonas* gingivalis was activated in the supplemented brain heart infusion broth, and cultured at 37° C. anaerobic condition (80% $N_2$, 10% $H_2$, 10% $CO_2$) for 24 hours to 48 hours.

5. Determination of Minimal Inhibitory Concentration (MIC)

Porphyromonas gingivalis was inoculated in the supplemented brain heart infusion broth at 37° C. anaerobic condition (80% $N_2$, 10% $H_2$, 10% $CO_2$) for 24 hours to 48 hours, and then diluted to $1 \times 10^8$ CFU/ml (T %=25% optical density 600), and the 195 μl broth was placed in ninety-six-well microplates. 5 μl of Antrodia camphorata 95% ethanol extract in dimethyl sulfoxide was added to the microplates to achieve final concentrations 1 μg/ml, 2 μg/ml, 4 μg/ml, 8 μg/ml and 16 μg/ml. Chlorhexidine was used as positive control. The 2.5% (v/v) dimethyl sulfoxide was used as normal control. After being cultured at 37° C. under anaerobic condition (80% $N_2$, 10% $H_2$, 10% $CO_2$) for 24 hours, microplates were measured by microplate reader at 600 nm, and the concentration at absorbance (Abs)≤0.5 was recognized as the minimal inhibitory concentration (Mi-Sun Kang et al., 2008, The journal of Microbiology, 744-750).

6. Determination of Minimal Bactericidal Concentration (MBC)

Porphyromonas gingivalis was inoculated in the supplemented brain heart infusion broth at 37° C. anaerobic condition (80% $N_2$, 10% $H_2$, 10% $CO_2$) for 48 hours, and then diluted to $1 \times 10^5$ CFU/ml (T %=25% optical density 600), and 195 μl broth was placed in ninety-six-well microplates. 5 μl of Antrodia camphorata 95% ethanol extract in dimethyl sulfoxide was added to microplates to achieve final concentrations 1 μg/ml, 2 μg/ml, 4 mg/ml, 8 mg/ml and 16 μg/ml. Chlorhexidine was used as positive control. Chlorhexidine was used as positive control. After Porphyromonas gingivalis with said solution of Antrodia camphorata 95% ethanol extract or chlorhexidine were cultured at 37° C. under anaerobic condition (80% $N_2$, 10% $H_2$, 10% $CO_2$) for 48 hours, 10 μl aliquot Antrodia camphorata 95% ethanol extract or chlorhexidine was added to supplemented brain heart infusion agar with 5% defibrinated sheep blood. Then, broth was gently coated uniformly onto supplemented brain heart infusion agar with 5% defibrinated sheep blood by a triangular sterilized glass rod and cultured at 37° C. anaerobic condition (80% $N_2$, 10% $H_2$, 10% $CO_2$) for 5 days. No colony growing concentration was recognized as the minimal bactericidal concentration. (Myrella Lessio Castro et al., 2009, Bioorganic & Medicinal Chemistry, 17:5332-5335)

7. Statistical Analysis

All results were expressed as the mean±standard error of the mean. Experiments were performed at least in triplicate. The Student's t-test was used to calculate the statistical significance of experimental results. Differences in data values were considered significant at $p<0.01$.

Example 1

Determination Of Minimal Inhibitory Concentration (MIC)

The objective of the present example uses the minimal inhibitory concentration described in said "Material and method" to determine the minimal inhibitory concentration of Antrodia camphorata 95% ethanol extract.

Figure 2:
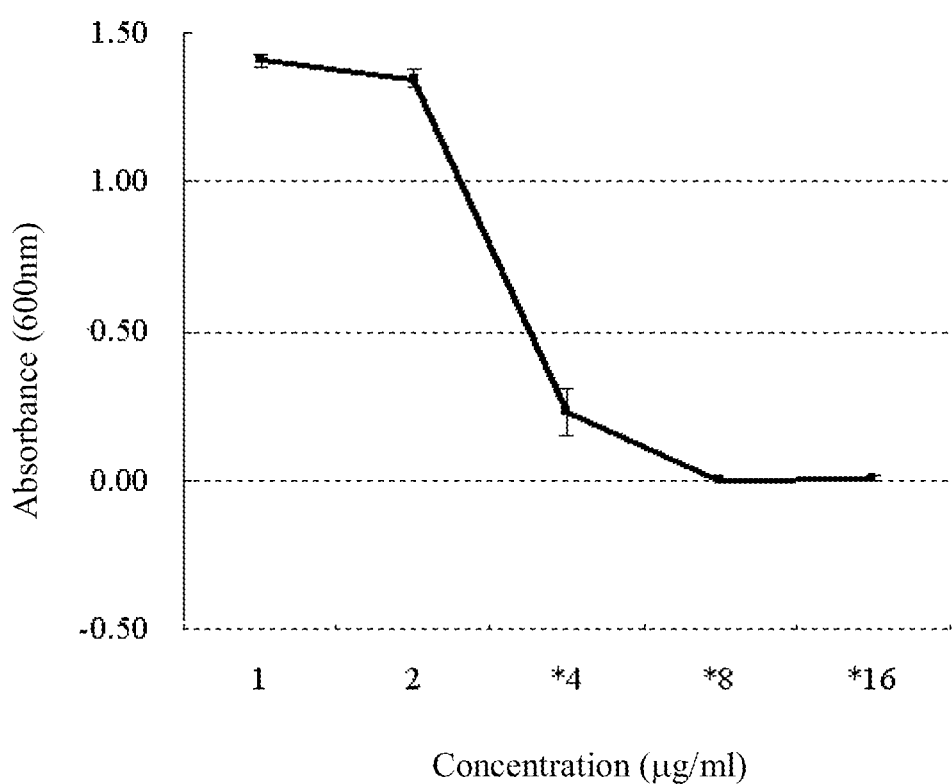
FIG. 2 illustrates the graph of inhibitory effect of chlorhexidine at various concentrations (1 µg/ml, 2 µg/ml, 4 µg/ml, 8 µg/ml and 16 µg/ml) on inhibiting *Porphyromonas gingivalis*.

The result is as shown in FIG. 1. When the concentration of Antrodia camphorata 95% ethanol extract is below 4 μg/ml, the absorption is higher than 0.5. As shown in FIG. 2, while the concentration of chlorhexidine as positive control is below 4 mg/ml, the absorption is higher than 0.5. Thus, the minimal inhibitory concentration of Antrodia camphorata 95% ethanol extract is 4 μg/ml, and the minimal inhibitory concentration of chlorhexidine as positive control is 4 μg/ml.

Example 2

Determination of Minimal Bactericidal Concentration (MBC)

Figure 3:
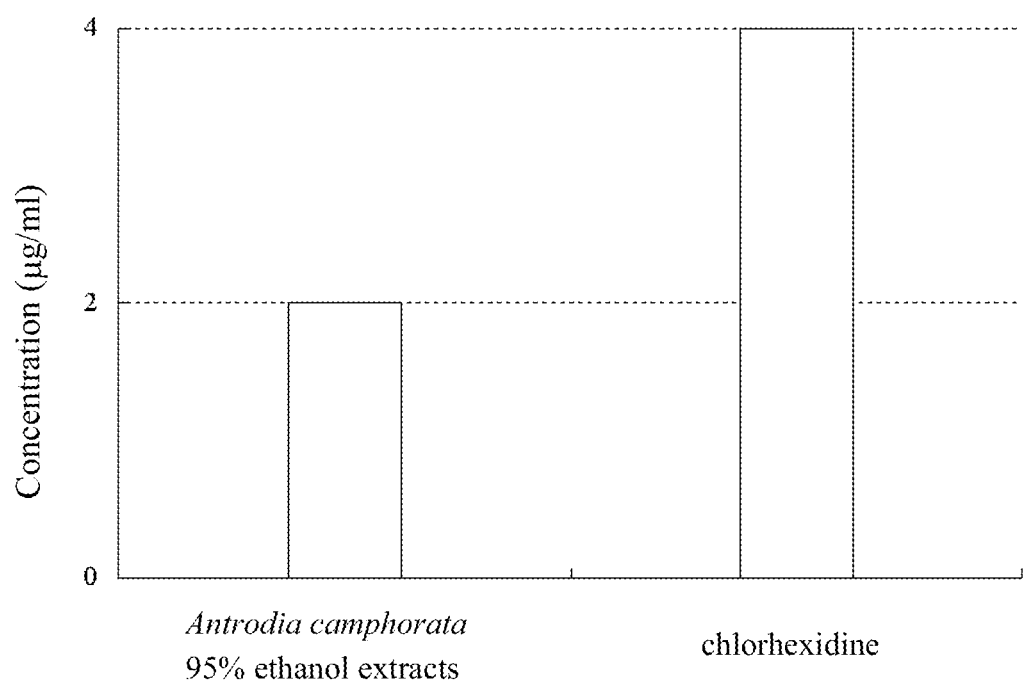
FIG. 3 is the bar chart of the minimal bactericidal concentration of *Antrodia camphorata* extract and chlorhexidine at various concentrations (2 µg/ml, 4 µg/ml) on inhibiting *Porphyromonas gingivalis*.

The objective of the present example uses the minimal bactericidal concentration described in said "Material and method" to determine the minimal bactericidal concentration of Antrodia camphorata 95% ethanol extract. The result is as shown in FIG. 3: there is no colony growing on the supplemented brain heart infusion agar with 5% defibrinated sheep blood while the concentration of Antrodia camphorata 95% ethanol extract is above 2 μg/ml. There is no colony growing on the supplemented brain heart infusion agar with 5% defibrinated sheep blood while the concentration of chlorhexidine is above 4 μg/ml.

TABLE 1

The minimal inhibitory concentration and minimal bactericidal concentration of Antrodia camphorata 95% ethanol extract and chlorhexidine for Porphyromonas gingivalis

| | Minimal inhibitory concentration (μg/ml) | Minimal bactericidal concentration (μg/ml) |
|---|---|---|
| Antrodia camphorata 95% ethanol extract | 4 | 2 |
| Chlorhexidine | 4 | 4 |

As shown in Table 1, the minimal bactericidal concentration of Antrodia camphorata 95% ethanol extract is 2 μg/ml; the minimal bactericidal concentration of chlorhexidine as positive control is 4 mg/ml. The result illustrates that Antrodia camphorata 95% ethanol extract have better efficacy for inhibiting or killing Porphyromonas gingivalis in comparison with the prior art.

Even though numerous characteristics and advantages of the present invention have been set forth in the foregoing description, together with details of the structure and features of the invention, the disclosure is illustrative only. Changes may be made in the details, especially in matters of shape, size, and arrangement of parts within the principles of the invention to the full extent indicated by the broad general meaning of the terms in which the appended claims are expressed.

What is claimed is:

1. A method of alleviating or treating Porphyromonas gingivalis induced periodontal disease, comprising:
    administrating to a subject with Porphyromonas gingivalis, in need thereof Porphyromonas gingivalis a therapeutically effective amount of a composition comprising an effective amount of an Antrodia camphorata powder or an extract of Antrodia camphorata, wherein said extract is an ethanol or aqueous ethanol extract, and wherein said composition inhibits or kills Porphyromonas gingivalis in said subject.

2. The method of claim 1, wherein the periodontal disease is selected from the group consisting of periodontitis and gingivitis.

* * * * *